United States Patent
Lizio et al.

(10) Patent No.: US 10,172,807 B2
(45) Date of Patent: Jan. 8, 2019

(54) NANOPARTICLE

(71) Applicant: Evonik Röhm GmbH, Darmstadt (DE)

(72) Inventors: Rosario Lizio, Dieburg (DE); Silko Grimm, Rossdorf (DE); Hans-Ulrich Petereit, Darmstadt (DE); Matthias Epple, Hattingen (DE); Gregor Doerdelmann, Haan (DE)

(73) Assignee: Evonik Röhm GmbH, Darmstadt (DE)

( * ) Notice: Subject to any disclaimer, the term of this patent is extended or adjusted under 35 U.S.C. 154(b) by 17 days.

(21) Appl. No.: 15/314,343

(22) PCT Filed: May 26, 2015

(86) PCT No.: PCT/EP2015/061538
§ 371 (c)(1),
(2) Date: Nov. 28, 2016

(87) PCT Pub. No.: WO2015/181138
PCT Pub. Date: Dec. 3, 2015

(65) Prior Publication Data
US 2017/0333361 A1 Nov. 23, 2017

(30) Foreign Application Priority Data
May 28, 2014 (EP) .................................. 14170333

(51) Int. Cl.
*A61K 48/00* (2006.01)
*C12N 15/88* (2006.01)
*A61K 9/51* (2006.01)
*A61K 9/14* (2006.01)
*A61K 9/50* (2006.01)
*C12N 15/11* (2006.01)
*A61K 9/00* (2006.01)
*A61K 31/7088* (2006.01)
*C12N 15/113* (2010.01)

(52) U.S. Cl.
CPC .......... *A61K 9/5115* (2013.01); *A61K 9/0019* (2013.01); *A61K 9/0053* (2013.01); *A61K 9/143* (2013.01); *A61K 9/5073* (2013.01); *A61K 9/5146* (2013.01); *A61K 9/5153* (2013.01); *A61K 9/5161* (2013.01); *A61K 9/5169* (2013.01); *A61K 9/5192* (2013.01); *A61K 31/7088* (2013.01); *C12N 15/111* (2013.01); *C12N 15/113* (2013.01); *C12N 15/88* (2013.01); *A61K 48/00* (2013.01); *C12N 2310/14* (2013.01); *C12N 2320/32* (2013.01)

(58) Field of Classification Search
CPC .. A61K 31/7088; A61K 48/00; A61K 9/0019; A61K 9/0053; A61K 9/5115; A61K 9/5146; A61K 9/5153; A61K 9/5161; A61K 9/5169; A61K 9/5192; C12N 15/113; C12N 2310/14; C12N 2320/32
See application file for complete search history.

(56) References Cited

U.S. PATENT DOCUMENTS

2013/0302342 A1  11/2013  Hartwig

FOREIGN PATENT DOCUMENTS

WO  WO2014/141288 A1 *  9/2014
WO  WO 2014/141288 A1   9/2014

OTHER PUBLICATIONS

Tang et al. Acta Pharmaceutica Sinica, vol. 48, No. 2, pp. 298-304. (2013).*
Tang et al. International Journal of Pharmaceutics, vol. 431, No. 1, pp. 210-221. (2012).*
International Search Report and Written Opinion dated Aug. 3, 2015 in PCT/EP2015/061538.
Extended European Search Report dated Dec. 5, 2014 in Patent Application No. 14170333.0.
Norihiro Watanabe, et al., "Transgenic Expression of a Novel Immunosuppressive Signal Converter on T Cells", Molecular Therapy, vol. 21, Supplement 1, XP055131645, 2013, p. S153.
Ping Zeng, et al. "Chitosan-modified poly(D,L-lactide-co-glycolide) nanospheres for plasmid DNA delivery and HBV gene-silencing", International journal of Pharmaceutics, vol. 415, XP028099873, 2011, pp. 259-266.
Jie Tang, et al., "Preparation and in vitro evaluation of pDNA-CaPi-PLGA nanoparticles with a core-shell structure", Database Medline, XP002732709, 2013, 2 Pages.
Jie Tang, et al., "Calcium phosphate embedded PLGA nanoparticles: A promising gene delivery vector with high gene loading and transfection efficiency", International journal of Pharmaceutics, vol. 431, XP028503199, 2012, pp. 210-221.
Mingzhen Zhang, et al., "Nano-structured composites based on calcium phosphate for cellular delivery of therapeutic and diagnostic agents", Nano Today, vol. 4, XP055153407, 2009, pp. 508-517.
U.S. Appl. No. 13/988,829, filed Jul. 29, 2013, US 2013-0302342 A1, dated Nov. 14, 2013, Benedikt Hartwig.

* cited by examiner

*Primary Examiner* — Janet L Epps-Smith
(74) *Attorney, Agent, or Firm* — Grüneberg and Myers PLLC

(57) ABSTRACT

The invention refers to a nanoparticle with a diameter which is the maximum in the nanoparticle size distribution, in the range of 10-300 nm, comprising a) a calcium phosphate nanoparticle core a), b) an active ingredient coating b) on the calcium phosphate nanoparticle core a), c) a lactic acid polymer coating c) on the active ingredient coating b), d) a cationic polymer coating d) on the lactic acid polymer coating c) selected from the group of polyethylene-imines, chitosan and human lactoferrin-derived peptides with a length of 14 to 30 amino acids.

16 Claims, No Drawings
Specification includes a Sequence Listing.

SEQUENCE LISTING

<160> NUMBER OF SEQ ID NOS: 8

<210> SEQ ID NO 1
<211> LENGTH: 22
<212> TYPE: PRT
<213> ORGANISM: Artificial Sequence
<220> FEATURE:
<223> OTHER INFORMATION: Synthetic peptide, SEQ ID NO: 3 in WO 2007/
      048599

<400> SEQUENCE: 1

Lys Cys Phe Gln Trp Gln Arg Asn Met Arg Lys Val Arg Gly Pro Pro
1               5                   10                  15

Val Ser Cys Ile Lys Arg

```
                        20

<210> SEQ ID NO 2
<211> LENGTH: 18
<212> TYPE: PRT
<213> ORGANISM: Artificial Sequence
<220> FEATURE:
<223> OTHER INFORMATION: Synthetic peptide, SEQ ID NO: 4 in WO 2007/
      048599

<400> SEQUENCE: 2

Cys Phe Gln Trp Gln Arg Asn Met Arg Lys Val Arg Gly Pro Pro Val
1               5                   10                  15

Ser Cys

<210> SEQ ID NO 3
<211> LENGTH: 16
<212> TYPE: PRT
<213> ORGANISM: Artificial Sequence
<220> FEATURE:
<223> OTHER INFORMATION: Synthetic peptide, SEQ ID NO: 5 in WO 2007/
      048599

<400> SEQUENCE: 3

Phe Gln Trp Gln Arg Asn Met Arg Lys Val Arg Gly Pro Pro Val Ser
1               5                   10                  15

<210> SEQ ID NO 4
<211> LENGTH: 11
<212> TYPE: PRT
<213> ORGANISM: Artificial Sequence
<220> FEATURE:
<223> OTHER INFORMATION: Synthetic peptide, SEQ ID NO: 6 in WO 2007/
      048599

<400> SEQUENCE: 4

Phe Gln Trp Gln Arg Asn Met Arg Lys Val Arg
1               5                   10

<210> SEQ ID NO 5
<211> LENGTH: 22
<212> TYPE: PRT
<213> ORGANISM: Artificial Sequence
<220> FEATURE:
<223> OTHER INFORMATION: Synthetic peptide, SEQ ID NO: 29 in WO 2007/
      048599

<400> SEQUENCE: 5

Lys Cys Arg Arg Trp Gln Trp Arg Met Lys Lys Leu Gly Ala Pro Ser
1               5                   10                  15

Ile Thr Cys Val Arg Arg
                20

<210> SEQ ID NO 6
<211> LENGTH: 18
<212> TYPE: PRT
<213> ORGANISM: Artificial Sequence
<220> FEATURE:
<223> OTHER INFORMATION: Synthetic peptide, SEQ ID NO: 30 in WO 2007/
      048599

<400> SEQUENCE: 6

Cys Arg Arg Trp Gln Trp Arg Met Lys Lys Leu Gly Ala Pro Ser Ile
1               5                   10                  15

Thr Cys
```

```
<210> SEQ ID NO 7
<211> LENGTH: 22
<212> TYPE: RNA
<213> ORGANISM: Artificial Sequence
<220> FEATURE:
<223> OTHER INFORMATION: Synthetic RNA, anti-eGFP siRNA, sense

<400> SEQUENCE: 7
gcaagcugac ccugaaguuc au                                              22

<210> SEQ ID NO 8
<211> LENGTH: 22
<212> TYPE: RNA
<213> ORGANISM: Artificial Sequence
<220> FEATURE:
<223> OTHER INFORMATION: Synthetic RNA, anti-eGFP siRNA, antisense

<400> SEQUENCE: 8
augaacuuca gggucagcuu gc                                              22
```

NANOPARTICLE

This application is a National Stage entry under § 371 of International Application No. PCT/EP2015/061538, filed on May 26, 2015, and claims priority to European Patent Application No. 14170333.0, filed on May 28, 2014.

FIELD OF THE INVENTION

The present application is concerned with calcium phosphate-lactic acid polymer-nanoparticles respectively combined nanoparticles for the delivery of active ingredients to living mammalian cells.

TECHNICAL BACKGROUND

Lactic acid polymers, like for instance poly(D,L-lactide-co-glycolide)copolymers (PLGA), are biodegradable polymers and well known in the art for example from EP1468035, U.S. Pat. No. 6,706,854, WO2007/009919A2, EP1907023A, EP2263707A, EP2147036, EP0427185 or U.S. Pat. No. 5,610,266.

US 2005/0053590A1 describes an endothelium-targeting nanoparticle for reversing endothelial dysfunction. A method for ameliorating cellular dysfunction comprises the steps of providing a composition that specifically targets a dysfunctional endothelial cell comprising a targeting ligand that binds specifically to an endothelial cell and a nucleic acid and delivering the composition to the cell under conditions that increase intracellular tetrahydrobiopterin concentration. The composition may further comprise a nanoparticle selected from a long list of suitable types of nanoparticles including calcium phosphate nanoparticles and biodegradable nanoparticles formulated from poly (D,L-lactide-co-glycolide)(PLGA) or combinations of the different nanoparticle types mentioned there.

WO 2007/048599 describes particulate drug delivery systems based on a polymeric carrier, characterized in that at least one signal substance for transport through a biological barrier and at least one active ingredient are included, with carrier, signal substance and active ingredient showing no covalent linkages with one another. The signal substance (cell penetrating peptide (CPP)) is lactoferrin or a peptide derived from lactoferrin.

In a particularly preferred embodiment, a signal peptide with the amino acid sequence KCFQWQRNMRKVRGPPVSCIKR (SEQ ID No.1 (=SEQ ID No. 3 in WO2007/048599)), CFQWQRNMRKVRGPPVSC (SEQ ID No.2 (=SEQ ID No. 4 in WO2007/048599)), FQWQRNMRKVRGPPVS (SEQ ID No.3 (=SEQ ID No. 5 in WO2007/048599)), FQWQRNMRKVR (SEQ ID No.4 (=SEQ ID No. 6 in WO2007/048599)), KCRRWQWRMKKLGAPSITCVRR (SEQ ID No.5 (=SEQ ID No. 29 in WO2007/048599)) and CRRWQWRMKKLGAPSITC (SEQ ID No.6 (=SEQ ID No. 30 in WO2007/048599))

or a derivative thereof.

In a preferred embodiment, the cell-penetrating peptides of WO 2007/048599 are comprising an amino acid sequence as shown in WO 2007/048599 in SEQ ID No. 3, SEQ ID No. 4, SEQ ID No. 29 or SEQ ID No. 30 or a corresponding sequence with an identity of at least 40%, preferably of at least 50%, particularly preferably with an identity of more than 75% or better of more than 90%.

WO 2007/076904A1 describes a peptide having an amino acid sequence comprising at least 8 consecutive amino acids of the human lactoferrin protein or of the bovine lactoferrin protein, whereby the peptide is suitable to act as a cell-penetrating peptide (CPP). Many of the peptides mentioned in WO 2007/076904A1 and in WO 2007/048599 are identical.

The most promising cell-penetrating peptide with the best effects in the examples is KCFQWQRNMRKVRGPPVSCIKR (SEQ ID No. 1 (=SEQ ID No. 3 in WO 2007/048599 and in WO 2007/076904A1)).

The lactoferrin-derived cell-penetrating peptides are intended to permit the transport of cargo molecules, which are active pharmaceutical ingredients such as DNA, RNA, peptides or antigens for vaccination, which may be orally ingested, through the biological membranes and thus allow an efficient uptake of these molecules in the human or animal organism.

WO2014/141288A1 (International publication date 18 Sep. 2014) describes a nanomaterial showing multi-functional properties such as radioactivity, raman scattering, near-infrared (NIR) fluorescence, para- or superparamagnetism and X-ray absorption. The multifunctional nanocontrast agent may have spherical or non-spherical shape and size ranging from 1-200 nm and can be delivered intravenously, intramuscularly or orally. The nanomaterial is based on calcium phosphate nanoparticles. The nanoparticles functions as multifunctional nanocontrast agent that may be conjugated or loaded with drug molecules such as bisphosphonates, chemodrugs, anticancer gene therapy agents, RNA fragments (siRNA, mi-RNA), photosensitive drugs, small molecule inhibitors, antibiotics. The calcium phosphate nanoparticles may be formulated in a polymeric shell of a biodegradable polymer containing the drugs. The biodegradable polymer may be among others a poly-lactic acid (PLA), poly(lactic-co-glycolic acid) (PLGA), polyethyleneimine (PEI), chitosan or carboxymethyl chitosan. The nanoparticles may be conjugated on their surface with targeting ligands such as including folic acid, antibodies, peptides, aptamers or carbohydrates. Capping agents such as citrate, polymers such as PEG, polyethyenimine, biphosphonates may be added.

Norihiro Watanabe et al. describe "Transgenic Expression of a Novel Immunosuppressive Signal Converter on T-cells", Molecular Therapy, vol. 21, 2013-05-01, p. s153-S153, (XP055131645).

Ping Zeng et al.: "Chitosan-modified poly/,-lactide-co-glycolide) nanospheres for plasmid DNA delivery and HBV gene silencing", International Journal of Pharmaceutics, Elsevier BV, NL, vol. 415, 2011-05-20, p. 259-266 (XP028099873, ISSN: 0378-5173). Ping Zeng et al describe nanoparticles formulated using poly(lactic-co-glycolic acid) (PLGA) for plasmid DNA (pDNA) delivery. Jie Tang et al. describes in Acta Pharmaceutica Sinica 2013, 48 (2): 298-304, the preparation and in vitro evaluation of calcium phosphate-pDNA nanoparticles (pDNA-CaPi) which are encapsulated in poly(lactid-co-glycolid)-copolymer (PLGA) in a core/shell (CS) structure. The core/shell structure particles (CS-pDNA-CaPi-PLGA-NPs) are compared to embedded CaPi modified PLGA nanoparticles (embedded-pDNA-CaPi-PLGA-NPs). The core/shell structure nanoparticles (CS-pDNA-CaPi-PLGA-NPs) were spherical in shape with an average particle size of 155+/−4.5 nm, zeta potentials of −0.38+/−0.1 mV, an entrapment efficiency of 80.56+/−2.5% and a loading efficiency of 1.16+/−0.04%. The core/shell structure particles were stable in the release media and could protect pDNA against nuclease degradation. They also exhibited sustained release of pDNA in vitro. The highest gene transfection efficiency of the CS-pDNA-CaPi-PLGA-NPs in vitro reached (24.66+/−0.46)% after 72 h transfection, which was significantly higher than that of free pDNA [(0.33+/−0.04)%, P<0.01] and the pDNA-PLGA-NPs [(1.5+/−0.07)%, P<0.01]. The transfection lasted for longer time than that of embedded-pDNA-CaPi-PLGA-NPs and the cytotoxicity was significantly lower than that of polyethylene-imine (PEI). Therefore CS-pDNA-CaPi-PLGA-NPs are supposed to be promising non-viral gene vectors.

Jie Tang et al: "Calcium phosphate embedded PLGA nanoparticles: A promising gene delivery vector with high gene loading and transfection efficiency", International Journal of Phramaceutics, Elsevier BV, NL, vol. 431, 2012-04-17, p. 210-221 (XP028503199, ISSN: 0378-5173). Jie Tang et al. describes the preparation and in vitro evaluation of calcium phosphate-pDNA nanoparticles (pDNA-CaPi) which are encapsulated in poly(lactid-co-glycolid)-copolymer (PLGA). The transfection efficiency of these nanoparticles on human embryotic kidney cells was found to be much higher with pDNA loaded PLGA nanoparticles or than with CaPi-pDNA embedded PLGA microparticles.

(Mingzehn Zang et al: Nano-structured composites based on calcium phosphatefor cellular delivery of therapeutic and diagnostic agents", Nano today, vol. 4, no. 6, 2009-12-01, p. 508-517 (XP055153407; ISSN: 1748-0132). The use of nanostructured calcium phosphate composites with emphasis on PEGylated calcium phosphate delivery systems especially for nucleic acids such as siRNA is described.

OBJECT AND SOLUTION

Tang J. et al. describes in Acta Pharmaceutica Sinica 2013, 48 (2): 298-304 the preparation and in vitro evaluation of calcium phosphate-pDNA nanoparticles (pDNA-CaPi-NP) which are encapsulated in poly(lactid-co-glycolid)-copolymer (PLGA) in a core/shell (CS) structure. The CS-pDNA-CaPi-PLGA-nanoparticles are supposed to be promising non-viral gene vectors.

It was an object of the invention to improve the delivery transfer efficiency of CS-pDNA-CaPi-PLGA-NPs in order to achieve vectors for the enhanced delivery of active ingredients, especially that of peptides proteins or nucleic acids to living cells. Another object was to enhance the siRNA-mediated gene silencing efficiency. At the same time the toxicity of the delivery vector should not be increased.

The object was solved by a nanoparticle, where the nanoparticle is combined from the components a), b), c) and d) as claimed and thus may be also called a "combined nanoparticle", with a diameter, which is the maximum in the nanoparticle size distribution, in the range of 10-300 nm, comprising
a) a calcium phosphate nanoparticle core a),
b) an active ingredient coating b) on the calcium phosphate nanoparticle core a),
c) a lactic acid polymer coating c) on the active ingredient coating b)
d) a cationic polymer coating d) on the lactic acid polymer coating c) selected from the group of polyethylene-imines, chitosan and human lactoferrin-derived peptides with a length of 14 to 30 amino acids.

DETAILED DESCRIPTION

Nanoparticle (Combined Nanoparticle)

The inventive nanoparticle is combined from the components a), b), c) and d) as claimed and thus may be called a "combined nanoparticle". The inventive nanoparticles may be of spherical shape. The nanoparticles may have an average diameter in the range of 10-600, 20-500, 50-250 nm, whereby the average diameter is preferably determined by Dynamic Light scattering (DLS, intensity %). The nanoparticles may have a diameter, which is the maximum in the nanoparticle size distribution (peak value), in the range of 10-300, 20-250, 80-150 nm, whereby the maximum in the nanoparticle size distribution is preferably determined by Dynamic Light scattering (DLS by number). The polydispersity index (DLS) of the nanoparticles may be in the range of 0-0.8, 0.05-0.7, 0.1-0.7, 0.3-0.7.

Calcium Phosphate Nanoparticle Core a)

The inventive nanoparticle comprises a calcium phosphate nanoparticle core a) with an active ingredient b) coated on there. The calcium phosphate nanoparticle core a) with an active ingredient b) coated on there may have an average diameter in the range of 10-400, 20-300, 50-200 nm. The average diameter is preferably determined by Dynamic Light scattering (DLS). The polydispersity index of the calcium phosphate nanoparticles core a) with an active ingredient b) coated on there may be in the range of 0-0.7, 0.05-0.7, 0.1-0.7, 0.3-0.7.

Active Ingredient Coating b)

The inventive nanoparticle comprises an active ingredient coating b) where an active ingredient is coated on the calcium phosphate nanoparticle a). An active ingredient coating is a coating which comprises or consists of an active ingredient. "Coated on" may also have the meaning of "associated with" or "associated on the surface" of the calcium phosphate nanoparticle. The calcium phosphate nanoparticle a) may be preferably stabilized by a coating layer of the active ingredient which prevents the agglomeration or further growth of the calcium phosphate nanoparticles. The coating or coating layer is attached to the surface of the calcium phosphate nanoparticles by ionic or electrostatic interaction.

A calcium phosphate nanoparticle core a) with an active ingredient coating b) may be prepared by mixing aqueous solutions comprising calcium ions and phosphate ions with addition, preferably in an aqueous solution, of an active ingredient for a residence (nucleation) time for at least 1, preferably 1-5 or 1-60 seconds. After or during the residence time calcium phosphate nanoparticles with the active ingredient coated on there are formed in the course of or after the precipitation process.

An active ingredient in the sense of the present application is a substance that may be delivered to a mammalian or human body in order to achieve a therapeutic effect and/or to cure a disease. Preferably the active ingredient is water-soluble. The active ingredient is preferably a peptide, a protein or a nucleic acid.

The active ingredient may be preferably a peptide, which is different from the human lactoferrin-derived peptide that may be used as cationic polymer coating d) and which is not considered as an active ingredient in the sense of the invention.

Examples for suitable peptides are for instance peptide hormones such as a human growth hormone.

Examples for suitable proteins are for instance antibodies, interleukins, interferons, protein based vaccines.

The active ingredient may be a nucleic acid, such as a double-stranded or single-stranded DNA or RNA, plasmid DNA (pDNA).

The active ingredient may be a siRNA (small interfering RNA).

The term "siRNA" is well known to a person skilled in the art. A typical siRNA may be defined as a double stranded RNA of about 19-23 base pairs length, in which single strands may overlap at the 3'-end for two nucleotides. siRNAs are cleavage products from large double-stranded RNAs such as cellular mRNA or RNA generated from viruses during their replication in living cells. These types of RNAs may be cut down to siRNAs for instance by the enzyme "Dicer", which is a type III RNase. siRNAs play an important role in post-transcriptional gene-silencing processes. Longer siRNAs, for instance 60 basepairs or longer, may also be synthesized by means of expression-vectors. Therefore siRNAs are of high interest to be used as active ingredients in order to achieve certain therapeutic effects and/or to cure certain diseases.

Lactic Acid Polymer Coating c)

The inventive nanoparticle comprises a lactic acid polymer coating c) on active ingredient coating b) respectively on the calcium phosphate nanoparticle core a) with the active ingredient b) coated thereon. A lactic acid polymer coating is a coating comprising, comprising essentially or consisting of a lactic acid polymer.

The calcium phosphate nanoparticle core a) with the active ingredient may be used as the inner water phase (W1) for a water-in-oil-in-water (W1/O/W2) emulsion, where the lactic acid polymer for the lactic acid polymer coating c) may be added in an organic solution to a water phase (W1) containing the calcium phosphate nanoparticle core a) with the active ingredient b) there under ultrasonic treatment to give a water in oil emulsion (W1/O) and where the water in oil emulsion (W1/O) may be added to an excess of another water phase (W2) under ultrasonic treatment to give the water-in-oil-in-water (W1/O/W2) emulsion, where the organic solvent may be removed to give a first dispersion, where the solid content of the first dispersion may be collected by centrifugation or tangential flow filtration may be re-dispersed in water and may be dried to give solid particles.

The term "Lactic acid polymer" shall mean polymers or copolymers comprising polymerized lactic acid or lactide units, preferably at least 10, at least 20, at least 30, at least 40, at least 50, at least 60, at least 70% by weight or up to 100% of polymerized lactic acid or lactide units. A lactide is a cyclic diester of lactic acid. The term lactide shall comprise L-lactide, D-lactide, or D,L-lactide. The polymerization of lactids to polylactic acid polymers may be performed by polycondensation under ring-opening conditions. Suitable comonomers that may be polymerized with the lactic acid or lactide respectively are glycolide, epsilon-caprolactone, trimethylene carbonate or dioxanone. Lactic acid polymers may include also an AB- or ABA-blockcopolymer containing an A-block selected from lactic acid polymers and a B-block selected from a polyethylenglycol polymer.

The lactic acid polymer preferably may be selected from lactic acid polymers or copolymers synthesized from monomer components or from a mixture of monomer components selected from the group consisting of a) to l):
a) D- and L-lactide,
b) L-lactide and glycolide,
c) D,L-lactide and glycolide,
d) L-lactide and epsilon-caprolactone,
e) L-lactide and dioxanone,
f) L-lactide and trimethylene carbonate,
g) L-lactide, D-lactide or D,L-lactide,
h) L-lactide,
i) DL-lactide,
j) statistically distributed monomer units of L-lactide, D-lactide or D,L-lactide and epsilon-caprolactone,
k) statistically distributed monomer units of L-lactide, D-lactide or D,L-lactide and dioxanone,
l) statistically distributed monomer units of L-lactide, D-lactide, or DL-lactide and trimethylene carbonate.

These kind of "lactic acid polymers" are biodegradable polymers and well known in the art for example from EP1468035, U.S. Pat. No. 6,706,854, WO2007/009919A2, EP1907023A, EP2263707A, EP2147036, EP0427185 or U.S. Pat. No. 5,610,266.

Preferably the lactic acid polymer is a lactide-glycolide copolymer.

Preferably the lactic acid polymer is a poly(D,L-lactide-co-glycolide) copolymer with an inherent viscosity IV from 0.1-2.0, 0.12-1.2, 0.14-1.0, 0.16-0.44, 0.16-0.24 [dL/g].

A preferred lactic acid polymer is a poly(D,L-lactide-co-glycolide) copolymer with a proportion of D,L-lactide:glycolide in the poly(D,L-lactide-co-glycolide) copolymer from 80:20 to 20:80, 70:30 to 30:70, 60:40 to 40:60 or 80:20 to 60:40 parts by weight, where the parts D,L-lactide:glycolide add up to 100 parts (100%).

Preferred lactic acid polymers are of the type of RESOMER® RG 502 (ester-end group) or RESOMER® RG 502 H (acid-end group) which are a poly(D,L-lactide-co-glycolide)-copolymers with a D,L-lactide:glycolide ratio of 45:55 to 55:45, preferred 50:50) and with an inherent viscosity IV in the range of 0.16-0.44 or 0.16-0.24 [dL/g].

The molecular weight ($M_w$) of the lactic acid polymers may be in the range of 1.000-1000.000, preferably in the range of 2.000-100.000, preferably in the range of 3.000 to 25.000 g/mol. Analytical methods to determine the molecular weight ($M_w$=average weight molecular weight) are well known to a skilled person. In general molecular weight $M_w$ can be determined by gel permeation chromatography or by a light-scattering method (see, for example, H. F. Mark et al., Encyclopedia of Polymer Science and Engineering, 2nd Edition, Vol. 10, pages 1 ff., J. Wiley, 1989).

The lactic acid polymer may be characterized by a glass transition temperature Tg from about 30 to 60, 35 to 55° C.

A lactic acid polymer is generally "bio-resorbable", which means that the polymer is broken down into oligomers in a slow hydrolytic reaction after implantation or injection in the human body or in the body of an animal in contact with the body fluids. Hydrolysis end products such as lactic acid or glycolic acid are metabolized into carbon dioxide and water. Other exchangeable expressions for the term "bio-resorbable polyester" which are often used are "resorbable polyester", "bio-degradable polyester" or "adsorptive polyester".

Cationic Polymer Coating d)

The combined nanoparticle comprises a cationic polymer coating d) on the lactic acid polymer coating c) selected from the group of polyethylene-imines, chitosanes and human lactoferrin-derived peptides with a length of 14-30 amino acids. A "cationic polymer coating" in the sense of the invention shall therefore mean a coating with a polymer, which contains one or more cationic groups respectively one or more cationic side groups or one or more groups or one or more side groups which may become cationic (positively charged) at least in a certain range of pH, preferably at a pH of 7.0 or below 7.0.

The dried solid particles, comprising the calcium phosphate nanoparticle core a) with the active ingredient b) coated on there and the lactic acid polymer coating c), may be re-dispersed in water and a cationic polymer for the cationic polymer coating d) may be added under stirring and incubation for at least 10 or 10-30 minutes to give a second dispersion which comprises the combined nanoparticle as solid content. The solid content of the second dispersion may be collected by centrifugation and re-dispersed or dried to result in an aqueous dispersion or a dry preparation comprising the combined nanoparticle.

Polyethylene-Imines

Polyethylene-imines may show a biological cell uptake promoting function which means when delivered simultaneously with an active ingredient (active pharmaceutical ingredient (API)) the polyethylene-imines facilitate and promote the uptake of the API in the cells.

Polyethylene-imine with lower molecular weight seem to provide a better transfection efficiency and seem to have a lower toxicity for the cells.

A preferred polyethylene-imine may have a molecular weight ($M_w$) in the range of 5.000 to 50.000, 20.000 to 30.000 g mol$^{-1}$.

Analytical methods to determine the molecular weight ($M_w$=average weight molecular weight) are well known to a skilled person. In general molecular weight $M_w$ can be determined by gel permeation chromatography or by a light-scattering method (see, for example, H. F. Mark et al., Encyclopedia of Polymer Science and Engineering, 2nd Edition, Vol. 10, pages 1 ff., J. Wiley, 1989).

Chitosan

The term chitosan shall include all different types of chitosan. Chitosan is a linear polysaccharides of randomly distributed β-(1-4)-linked D-glucosamine and N-acetyl-D-glucosamine. Chitosan may be gained from shrimp or other crustacean shells by treatment with the alkali sodium hydroxide.

A suitable chitosan may be a low molecular weight chitosan preferably with a molecular weight (Mw) of about 20.000 to 250.000, more preferably 40.000-200.000 dalton. This has the advantage that the size of the resulting nanoparticles may be directed to a smaller size. A suitable chitosan may be acetylized to a degree of 50 to 100, preferably 70-90%.

Human Lactoferrin-Derived Peptide (HLf).

Human lactoferrin-derived peptides may show a biological cell penetrating function (cell penetrating peptide (CPP), s. for instance WO 2007/048599 or WO 2007/076904A1) which means when delivered simultaneously with an active pharmaceutical ingredient (API) to human cells the human lactoferrin-derived peptides facilitates and promotes the uptake of the API in the cells.

The Human lactoferrin-derived peptide may show an amino acid sequence which is found with a similarity of at least 50, 60, 70, 80, 90 or 100% to the amino acid sequence of the native human lactoferrin protein within the sequence region which is codes for its cell penetrating function.

The Human lactoferrin-derived peptide is a cationic polymer which contains one or more amino acids with side groups that may become cationic (positively charged in an aqueous environment) at least at pH 7 or below pH 7 (for instance arginine (R) or lysine (K)). The Human lactoferrin-derived peptide itself is not regarded as an active ingredient in the sense of the invention.

The human lactoferrin-derived peptide may have a length of 14 to 30, 19 to 30, 20 to 25, 21 to 23 or 22 amino acids. Preferably the amino acid sequence of the human lactoferrin-derived peptide may include at least two or two cysteine residues.

Preferably the amino acid sequence of the human lactoferrin-derived peptide may include at least two or two cysteine residues that may form an internal cystein-cystein-bridge (cystin-bridge). Preferably two cysteine residues are present in oxidized form, forming an internal cystin-bridge.

A suitable human lactoferrin-derived peptide may have a length of 14 to 30, 19 to 30, 20 to 25, 21 to 23 or 22 amino acids and may contain at least 4, at least 6, 4 to 8, 5 to 7 or 6 amino acids with, at or below pH 7, positively charged side chains, preferred arginine and/or lysine.

A suitable human lactoferrin-derived peptide may have a length of 14 to 30, 19 to 30, 20 to 25, 21 to 23 or 22 amino acids and may include an amino acid sequence according to SEQ. ID. No. 1 KCFQWQRNMRKVRGPPVSCIKR or a sequence which does not differ in more than 8, 7, 6, 5, 4, 3, 2 or 1 amino acid positions from the sequence SEQ. ID. No. 1.

The term "differ in an amino acid position" shall be understood in the sense that there is, compared to the sequence SEQ. ID. No. 1, a different amino acid present in a certain position or there is no amino acid in a certain position or there is an additional amino acid present within the sequence or added to the sequence or any combination of these cases.

Most preferably the human lactoferrin-derived peptide does not differ in more than 8, 7, 6, 5, 4, 3, 2 or 1 amino acid positions from the sequence SEQ. ID. No. 1 whereby at least two cysteine or two cystein residues are present, preferably two cystein according to positions 2 and 19 of SEQ. ID. No. 1 are present. Preferably the cystein residues are present in oxidized form, forming an internal cystein-cystein-bridge (cystin-bridge).

The human lactoferrin-derived peptide may be preferably a peptide with the amino acid sequence according to SEQ. ID. No. 1 KCFQWQRNMRKVRGPPVSCIKR or a sequence which is at least 80 or 90% homologous to that sequence. Preferably the cysteine residues in positions 2 and 19 of SEQ. ID. No. 1 or in similar or according positions are present.

Pharmaceutical Composition

The application further discloses a pharmaceutical composition comprising the nanoparticle, which is a combined nanoparticle as explained before.

Process for Preparing a Combined Nanoparticle

The application further discloses a process for preparing the inventive nanoparticle respectively the combined nanoparticle.

The process for preparing a combined nanoparticle may be preferably carried out in that the calcium phosphate nanoparticle core a) is prepared by mixing an aqueous solution comprising calcium ions with an aqueous solution comprising phosphate ions preferably for at least 1 or 1-3, or 1-60 seconds with the addition of the active ingredient b) before, during or preferably after mixing, to give a calcium phosphate nanoparticle core a) with the active ingredient coating b). An aqueous solution comprising calcium ions may be an aqueous solution comprising of water soluble calcium salts, e.g. calcium chloride ($CaCl_2$), calcium-L-lactate ($Ca(CH_3$—HCOH—$COO)_2$) or calcium nitrate ($Ca(NO_3)_2$). An aqueous solution comprising phosphate ions may be an aqueous solution comprising a water soluble phosphate salt, e.g. sodium hydrogen phosphate ($Na_2HPO_4$) or di-ammonium hydrogen phosphate ($(NH_4)_2HPO_4$).

The two aqueous solutions may be brought together first in an Y-adapter, preferably with a length of 5 to 20 mm, where the mixed solutions may have a residence (nucleation) time of at least 1 or 1-3, or 1-60, preferably at flow rates of 10 to 30 µl/sec, before they are mixed continuously (for instance by a Vortex®).

Preferably the aqueous solution comprising calcium ions does not comprise phosphate ions. Preferably the aqueous solution comprising phosphate ions does not comprise calcium ions.

The active ingredient, preferably a water soluble active ingredient, such as a peptide, a protein, a DNA or a RNA, a siRNA, (small interfering RNA) may be added already to one or to both of the aqueous solutions comprising calcium ions or phosphate ions before, during or after the mixing of these solutions.

The mixed aqueous solution comprising calcium ions and phosphate ions and the active ingredient, may be used as the inner water phase 1 (W1=water phase 1) for a water-in-oil-in-water (W1/O/W2) emulsion (O=oil phase, W2=water phase 2), where the lactic acid polymer for the polymer coating c) is added in an organic solution to a water phase (W1), preferably by ultrasonic treatment, to give an water-in-oil emulsion (W1/O) and where the water-in-oil emulsion (W1/O) is added, to a further water phase 2 (W2), preferably to an excess (excess volume) of a further water phase 2 (W2), preferably by ultrasonic treatment, to give the water-in-oil-in-water (W1/O/W2) emulsion, where the organic solvent is removed to give a first dispersion, where the solid content of the first dispersion is collected, preferably by centrifugation, re-dispersed in water and dried to give solid particles, where the dried solid particles are re-dispersed in water and a cationic polymer for the a cationic polymer coating d) is added under stirring, preferably with an incubation time for at least 10 minutes, to give a second dispersion which comprises the combined nanoparticle as solid content, where the solid content of the second dispersion may be collected by centrifugation and re-dispersed or dried to result in an aqueous dispersion or a dry preparation comprising the combined nanoparticle.

Use

The application further discloses the use of the inventive nanoparticle in a method of preparing a pharmaceutical composition suitable for the oral or parenteral delivery of the active ingredient included in the nanoparticle.

EXAMPLES

Materials

PLGA=Poly(D,L-lactide-co-glycolide) 50:50 (Resomer® RG 502 H, $M_w$=7,000-17,000 g mol$^{-1}$, Evonik Industries AG (Darmstadt)). Polyvinyl alcohol (PVA, $M_w$=30,000-70,000 g mol$^{-1}$, 87-90% hydrolyzed), chitosan (low molecular weight, 75-85% deacetylated) and polyethyleneimine (PEI, $M_w$=25,000 g mol$^{-1}$) were purchased from Sigma-Aldrich. For gene-silencing experiments with anti-eGFP-siRNA (eGFP=enhanced Green Fluorescent Protein), desalted, double-stranded siRNA from Invitrogen, Ambion® (Carlsbad, USA), sense, 5"-GCAAGCUGACCCUGAAGUU-CAU-3"(SEQ ID No. 7) and antisense, 5"-AUGAAC-UUCAGGGUCAGCUUGC-3" (SEQ ID No. 8) ($M_w$=14,019.5 g mol$^{-1}$) was used. For transfection experiments with plasmid DNA, pcDNA3-eGFP encoding for enhanced fluorescent protein (eGFP) was isolated from *Echerichia coli* using a Nucleobond endotoxin-free plasmid DNA kit (Macherey-Nagel, Dueren, Germany). All other chemicals were of analytical grade and used without further purification.

The human lactoferrin-derived peptide (HLf) used in the examples was a synthesized peptide with an amino acid sequence according to SEQ. ID. No. 1 KCFQWQRNMRK-VRGPPVSCIKR.

Instruments

For the formation of water-in-oil and water-in-oil-in-water emulsions, sonication (ultrasonic) was carried out with a Hielscher UP50H instrument, sonotrode MS2, 70% amplitude, pulse 0.7, for 20 s. Dynamic light scattering and zeta potential determinations were performed with a Zeta-sizer nanoseries instrument (Malvern Nano-ZS, laser: $\lambda$=532 nm) using the Smoluchowski approximation and taking the data from the Malvern software without further correction. The particle size data refer to scattering intensity distributions (z-average). Confocal laser scanning microscopy was performed with a confocal laser scanning microscope (SP5 LCSM, Leica) with a 63× water objective. Centrifugation was performed at 4° C. with a Heraeus Fresco 21 instrument (Thermo Scientific). Transfection and gene silencing efficiencies were determined by transmission light and fluorescence spectroscopy with a Carl Zeiss Axiovert 40 CFL instrument. The viability of the cells was analyzed by the MTT-Test by spectrophotometric analysis with a Multiscan FC instrument (ThermoFisher scientific, Vantaa, Finland) a $\lambda$=570 nm. Freeze-drying was performed with a Christ, Alpha 2-4 LSC instrument.

Examples Overview

Example 1: Synthesis of calcium phosphate (CaP)-active ingredient nanoparticles
  Example 1a: Synthesis of CaP-eGFP-DNA nanoparticles
  Example 1b: Synthesis of CaP-anti-eGFP-siRNA nanoparticles
Example 2: Synthesis of CaP-active ingredient-PLGA-nanoparticles
  Example 2a: Synthesis of CaP-(FITC-BSA)-PLGA nanoparticles
  Example 2b: Synthesis of CaP-anti-eGFP-siRNA nanoparticles
  Example 2c: Synthesis of CaP-eGFP-DNA-PLGA nanoparticles
Example 3: Synthesis of CaP-anti-eGFP-siRNA-PLGA-cationic polymer nanoparticles
  Example 3a: Synthesis of CaP-anti-eGFP-siRNA-PLGA-PEI nanoparticles
  Example 3b: Synthesis of CaP-anti-eGFP-siRNA-PLGA-chitosan nanoparticles
  Example 3c: Synthesis of CaP-anti-eGFP-siRNA-PLGA-HLf nanoparticles
Example 4: Cellular Uptake (HeLa-cells)
Example 5: Gene silencing Example 1: Synthesis of CaP-Active Ingredient Nanoparticles Calcium phosphate nanoparticles were synthesized with a rapid precipitation method. The nucleic acids adsorb on the surface of the calcium phosphate nanoparticles. Hence, crystal growth is inhibited and the calcium phosphate nanoparticles are electrosterically stabilized. In this case DNA or siRNA act both as active ingredient and as stabilizing agent that protects the dispersion from aggregation.

Example 1a: Synthesis of CaP-eGFP-DNA Nanoparticles

Aqueous solutions of calcium nitrate (6.25 mM, 105 µL) and di-ammonia-hydrogen-phosphate (3.74 mM, 105 µL)

were mixed through a Y-adapter in a tube reactor with a syringe pump and pumped under continuous mixing (Vortex) into an aqueous solution of eGFP-DNA (2.5 mg mL$^{-1}$, 40 μL). The flow rate of the solutions was 16.6 μL s$^{-1}$, and the residence (nucleation) time in the Y-adapter (7 mm length) was 1.3 s. After the completed precipitation, the dispersion of the nanoparticles (core: calcium phosphate; shell: nucleic acid) was cooled with ice and used after 5 min of incubation for the encapsulation into PLGA nanoparticles.

Example 1b: Synthesis of CaP-anti-eGFP-siRNA Nanoparticles

Aqueous solutions of calcium nitrate (6.25 mM, 105 μL) and di-ammonia-hydrogen-phosphate (3.74 mM, 105 μL) were mixed through a Y-adapter in a tube reactor with a syringe pump and pumped under continuous mixing (Vortex) into a solution of anti-eGFP-siRNA (3.9 mg mL$^{-1}$, 40 μL). The flow rate of both solutions was 16.6 μL s$^{-1}$, and the residence (nucleation) time in the Y-adapter (7 mm length) was 1.3 s. After the completed precipitation, the dispersion of the nanoparticles (core: calcium phosphate; shell: nucleic acid) was cooled with ice and used after 5 min of incubation for the encapsulation into PLGA nanoparticles.

Example 2: Synthesis of CaP-Active Ingredient-PLGA Nanoparticles

To protect the outer shell of DNA or siRNA from degrading enzymes like DNases or RNases and to provide a sustained release profile to the particles, the calcium phosphate-DNA or calcium phosphate-siRNA nanoparticles were then encapsulated into a matrix of PLGA in examples 2b respectively 2c. The aqueous calcium phosphate-DNA or calcium phosphate-siRNA dispersion was used as the inner aqueous phase (W1) in the emulsion process. The polymer was dissolved in dichloromethane (O). Sonication leads to the primary W1/O emulsion with fine water droplets (containing the calcium phosphate nanoparticles) in the oil phase. Addition to the continuous water phase (PVA in water) and subsequent sonication leads to a stable W1/O/W2-emulsion. Evaporation of the organic solvent under reduced pressure yields an almost transparent dispersion.

Example 2a: Synthesis of CaP-(FITC-BSA)-PLGA Nanoparticles

The nanoparticles should be marked with FITC-BSA (fluorescein isothiocyanate labeled bovine serum albumin) in order to show the cellular-uptake of the nanoparticles by fluorescence. For the functionalization with the marker molecule FITC-BSA calcium phosphate was therefore precipitated during the emulsion process in the primary W1/O-emulsion. This was necessary because FITC-BSA adsorbs to calcium phosphate nanoparticles but does not colloidally stabilize them (unless DNA or RNA).

Two W1/O-emulsions (A and B) were prepared in a first step. Emulsion A contained the phosphate salt solution and the biomolecule in the inner water droplets and PLGA was dissolved in the organic phase. Emulsion B contained the calcium salt solution in the inner aqueous phase and also PLGA dissolved in the organic phase. Mixing both emulsions under sonication led to the precipitation of calcium phosphate in the inner water droplets. Addition of the combined W1/O-emulsions into the continuous water phase (PVA in water) and sonication led to a stable W1/O/W2- emulsion. Evaporation of the organic solvent under reduced pressure gave an almost transparent, yellow dispersion. With this method, crystal growth was limited by the small volume of the water droplet (microreactor) in the organic solvent.

Calcium phosphate-FITC-BSA-PLGA nanoparticles were synthesized by a W1/O/W2 emulsion solvent evaporation method. First, two W/O emulsions (A and B) were prepared by ultrasonication. For emulsion A, 625 μg FITC-BSA was dissolved in 125 μL of a 10 mM solution of Na$_2$HPO$_4$. This was dispersed in a solution of PLGA in dichloromethane (13.3 mg mL$^{-1}$, 375 μL). For emulsion B, 625 μg FITC-BSA was dissolved in 125 μL of a 1.25 M solution of CaCl$_2$ (1.25 M, 125 μL). This was dispersed in a solution of PLGA in dichloromethane (13.3 mg mL$^{-1}$, 375 μL). Then, emulsions A and B were mixed by sonication (10 s) to form emulsion C. This W$_1$/O-emulsion was then added dropwise to the continuous water phase (3 mL), containing 30 mg PVA as dispersant, and sonicated again (sonotrode) to form a yellow, milky W1/O/W2-emulsion. After removal of dichloromethane under reduced pressure (200-600 mbar), the calcium phosphate-FITC-BSA nanoparticles were incorporated into the PLGA particle. An excess of PVA and FITC-BSA was removed by centrifugation (30 min at 14,800 rpm) and redispersion of the particles in ultrapure water for three times by sonication (sonotrode). To determine the encapsulation efficiency of FITC-BSA, the supernatants were analyzed by UV/Vis spectroscopy at 460 nm after previous calibration with dissolved FITC-BSA. The resulting dispersion was shock-frozen in liquid nitrogen and finally lyophilized for 72 h at 0.31 mbar and −10 C. The particles were easily redispersible in water by gentle shaking.

The calcium phosphate-PLGA nanoparticles contained 5% calcium phosphate as determined by atomic absorption spectroscopy (computed from the content of calcium).

Example 2b: Synthesis of CaP-Anti-eGFP-siRNA-PLGA Nanoparticles

For the encapsulation of anti-eGFP-siRNA-functionalized calcium phosphate nanoparticles into PLGA nanoparticles, a water-in-oil-in-water (W1/O/W2) double emulsion solvent evaporation method was applied. To a solution of 10 mg PLGA dissolved in 750 μL dichloromethane, 250 μL of the dispersion of calcium phosphate/nucleic acid nanoparticles from example 1b was added. Then a solution of 200 μg RNase-free acetylated bovine serum albumin (BSA) in 40 μL water as dispersant was added. The mixture was sonicated (sonotrode, 15 s) to form the primary, milky white W1/O-emulsion. The W1/O-emulsion was then immediately poured into the continuous water phase (3 mL), containing 30 mg polyvinyl alcohol (PVA) as dispersant, and ultrasonicated again (sonotrode, 15 s).

Finally, the PLGA nanoparticles were precipitated after the dichloromethane was removed under reduced pressure (200-600 mbar) in a rotary evaporator. Thereby, the calcium phosphate nanoparticles carrying siRNA were incorporated into a nanoparticulate matrix of PLGA. The excess of PVA was removed by centrifugation (30 min at 14,800 rpm) and redispersion of the particles in ultrapure water for three times. To determine the encapsulation efficiency of the nucleic acids, the remaining supernatants were analyzed by UV/Vis spectroscopy at 260 nm according to standard protocols. The resulting dispersion was shock-frozen in liquid nitrogen and finally lyophilized for 72 h at 0.31 mbar and −10° C. The particles were easily redispersible in water by gentle shaking.

Example 2c: Synthesis of CaP-eGFP-DNA-PLGA Nanoparticles

For the encapsulation of eGFP-DNA-functionalized calcium phosphate nanoparticles into PLGA nanoparticles, a water-in-oil-in-water (W1/O/W2) double emulsion solvent evaporation method was applied. To a solution of 10 mg PLGA dissolved in 750 μL dichloromethane, 250 μL of the dispersion of calcium phosphate/nucleic acid nanoparticles from example 1a was added. Then 40 μL of a solution of 20 mg/ml RNase-free acetylated bovine serum albumin (BSA) in water was added as dispersant. The mixture was sonicated (sonotrode, 15 s) to form the primary, milky white W1/O-emulsion. The W1/O-emulsion was then immediately poured into the continuous water phase (3 mL), containing 30 mg polyvinyl alcohol (PVA) as dispersant, and sonicated again (sonotrode, 15 s).

Finally, the PLGA nanoparticles were precipitated after the dichloromethane was removed under reduced pressure (200-600 mbar) in a rotary evaporator. Thereby, the calcium phosphate nanoparticles carrying DNA were incorporated into a nanoparticulate matrix of PLGA. The excess of PVA was removed by centrifugation (30 min at 14,800 rpm) and redispersion of the particles in ultrapure water for three times. To determine the encapsulation efficiency of the nucleic acids, the remaining supernatants were analyzed by UV/Vis spectroscopy at 260 nm according to standard protocols. The resulting dispersion was shock-frozen in liquid nitrogen and finally lyophilized for 72 h at 0.31 mbar and −10° C. The particles were easily redispersible in water by gentle shaking.

Example 3: Synthesis of CaP-siRNA-PLGA-Cationic Polymer Nanoparticles

To enhance the cellular uptake of the calcium phosphate-PLGA nanoparticles, the surface charge can be reversed by layer-by-layer deposition of cationic polymers like chitosan, PEI and HLf. Furthermore, the polymers (Chitosan and PEI) are capable to induce the proton sponge effect. This leads to an enhanced endosomal escape of the nanoparticles and an increased therapeutic efficiency. As shown by zeta potential measurements, the surface charge of the calcium phosphate-PLGA nanoparticles could be easily reversed by layer-by-layer deposition of cationic polymers from about −24 mV to +50 mV (chitosan), to +31 mV (PEI) or +10 mV (HLf). SEM images of HLf modified CaP-siRNA-PLGA particles show spherical nanoparticles. The size and morphology of the nanoparticles did not change significantly.

Example 3a: Synthesis of CaP-siRNA-PLGA-PEI Nanoparticles 1.5 mg of the freeze-dried particles from example 2b were resuspended in 1 mL ultrapure water and added dropwise to an aqueous PEI solution (2 mg in 1 mL) under continuous stirring. After 30 min of continuous stirring at room temperature, the dispersion was purified three times by centrifugation (30 min at 14,800 rpm) and redispersion (shaking, no sonication necessary) in ultrapure water. For cell culture experiments, the particles were finally redispersed in the cell culture medium.

Example 3b: Synthesis of CaP-siRNA-PLGA-Chitosan Nanoparticles 1.5 mg of the freeze-dried particles from example 2b were resuspended in 1 mL ultrapure water and added dropwise to an aqueous chitosan solution (5 mg in 1 mL, pH adjusted to 5 with acetic acid) under continuous stirring. After 30 min of continuous stirring at room temperature, the dispersion was purified three times by centrifugation (30 min at 14,800 rpm) and redispersion (shaking, no sonication necessary) in ultrapure water. For cell culture experiments, the particles were finally redispersed in the cell culture medium.

Example 3c: Synthesis of CaP-siRNA-PLGA-HLf Nanoparticles 3 mg freeze dried particles from example 2b were resuspended in 3 ml ultrapure water and added in 3 ml (2 mg/ml) solution of human lacto ferrin for 2 h, under continuous stirring. The treated particles were freeze dried. For cell culture experiments, the particles were redispersed and purified in ultrapure water and by centrifugation (30 min at 14,800 rpm) and finally redispersed in the cell culture medium.

Example 4: Cellular Uptake (HeLa)

HeLa cells were cultivated in Dulbecco's modified Eagle's medium (DMEM) supplemented with 10% fetal calf serum (FCS), 100 U mL$^{-1}$ penicillin, and 100 U mL$^{-1}$ streptomycin at 37° C. under 5% $CO_2$ atmosphere.

Cellular uptake experiments were done with cells, which are seeded and cultivated in 8-well plates for 24 h before use. CaP-(FITC-BSA)-PLGA nanoparticle solution (unmodified (example 2b), modified with chitosan, PEI or HLf (example 3)) were added to the cells for 1 hour and 3 hour. For fluorescence microscopy the cell nucleus were colored with DAPI. The fluorescence microscope images show clearly that modified CaP-(FITC-BSA)-PLGA nanoparticles were efficiently taken up by the HeLa cells. While PEI modified CaP-(FITC-BSA)-PLGA nanoparticles were accumulate efficiently after 1 hour, the uptake of chitosan or HLf modified CaP-(FITC-BSA)-PLGA nanoparticles could be shown efficiently after 3 hours.

For co-localization experiments, HeLa cells were seeded in 8-well plates (Lab-Tek) and cultivated for 24 h. Then, HeLa cells were transfected with 50 ng of Lamp1-RFP plasmid-DNA and 0.3 μl Lipofectamine 2000 (Life technology) according to the manufacturer's instructions. After 4 h, the cell culture medium was changed and the cells were washed for several times with phosphate buffered saline (PBS). After additional 16 h, cells were treated with the nanoparticle dispersion (20 μL, 1 mg nanoparticles mL$^{-1}$) and examined with a confocal laser scanning microscope at different time points.

Cellular uptake studies of calcium phosphate-(FITC-BSA)-PLGA nanoparticles and co-localization experiments with Lamp1-RFP expressing HeLa cells showed that the nanoparticles were efficiently taken up by the cells. Nanoparticles with a negative surface charge had a low affinity to the cell membrane and were only moderately taken up, while nanoparticles with a positive surface charge (chitosan- or PEI-functionalized nanoparticles) covered the cell membrane after 1 h of incubation due to electrostatic interactions of the negatively charged cell membrane and the cationic surface of the nanoparticles. In addition, the majority of the negatively charged calcium phosphate-(FITC-BSA)-PLGA nanoparticles ended up in the endosome as shown by the co-localization of Lamp1-RFP and the green fluorescence of FITC-BSA. In contrast, chitosan- and PEI-functionalized calcium phosphate-(FITC-BSA)-PLGA nanoparticles (positive surface charge) induced the proton sponge effect and escaped the endosome as shown by a diffuse green fluorescence in the cytosol after 3 h of incubation.

Example 5: Gene Silencing

HeLa-eGFP cells (genetically modified HeLa cells that expressed enhanced green fluorescent protein, eGFP) were cultivated in DMEM supplemented with 10% FCS (fetal calf serum), 100 U mL$^{-1}$ penicillin, 100 U mL$^{-1}$ streptomycin, and 50 μg mL$^{-1}$ geneticin at 37° C. and 5% $CO_2$ atmosphere. 12 h before the addition of the nanoparticles, the cells were trypsinized and seeded in 24-well plates with a density of either 2.5·10$^4$ cells per well.

Before the transfection, the cell culture medium was replaced by the nanoparticles redispersed in fresh cell culture medium (0.1 mg nanoparticles in 0.5 mL corresponding to 0.8 μg-1 μg siRNA per well). After incubation for 7 h, the transfection medium was replaced by fresh cell culture medium. The efficiency of the gene silencing was measured 72 h after the addition of the nanoparticles by light microscopy and fluorescence microscopy.

As control, the cells were transfected with Lipofectamine™ 2000 as recommended by the manufacturer. In brief, 50 μL of DMEM (without FCS) was mixed with 1 μL Lipofectamine™ 2000 and incubated for 5 min at room temperature. Anti-eGFP-siRNA (20 pmol, 0.28 μg) was added to 50 μL of DMEM (without FCS). Then, both solutions were mixed and incubated for 20 min before 100 μL of this solution and additionally 400 μL of DMEM were added to each well. After incubation for 7 h, the transfection medium was replaced by fresh cell culture medium.

The efficiencies of the gene silencing experiments with anti-eGFP-siRNA functionalized calcium phosphate-PLGA nanoparticles were calculated from fluorescence microscopy images and were calculated as follows:

$$\frac{\text{not fluorescing cells after transfection [\%]} - \text{not fluorescing cells in control [\%]}}{\text{fluorescing cells in control [\%]}} * 100$$

HeLa-eGFP cells cultivated under the same conditions but without any treatment were used as control.

Calcium phosphate-PLGA nanoparticles functionalized with anti-eGFP-siRNA efficiently knocked down the eGFP-coding gene in eGFP-expressing HeLa cells. The cationic calcium phosphate-PLGA-siRNA nanoparticles coated with either chitosan, PEI or HLf showed gene silencing efficiencies of 28, 50 or 51% respectively. In accordance to the transfection experiments, the vitality of the cells after the treatment with calcium phosphate-PLGA nanoparticles was in the range or even higher in comparison to liposomal transfection agents such as Lipofectamine®. The cationic calcium phosphate-PLGA-siRNA nanoparticles coated with either chitosan, PEI- or HLf showed good cell viability, although PEI is known for its cytotoxicity. The results are summarized in table 1.

TABLE 1

|  | Diameter (Maximum in the nanoparticle size distribution by DLS (by number)) [nm] | Polydispersity index by DLS | Zeta Potential by DLS [mV] | Cell viability [%] | Gene silencing efficiency [%] |
| --- | --- | --- | --- | --- | --- |
| Lipofectamine | — | — | — | 73 | 74 |
| CaP-siRNA-PLGA | 105 | 0.35 | −25 | 80 | 22 |
| CaP-siRNA-PLGA-chitosan | 106 | 0.42 | +52 | 85 | 28 |
| CaP-siRNA-PLGA-PEI | 91 | 0.38 | +32 | 72 | 50 |
| CaP-siRNA-PLGA-HLf | 122 | 0.60 | +3 | 76 | 51 |

The invention claimed is:

1. A nanoparticle with a diameter, which is the maximum in the nanoparticle size distribution, in the range of 10-300 nm, the nanoparticle comprising:
 a calcium phosphate nanoparticle core a),
 an active ingredient coating b) on the calcium phosphate nanoparticle core a),
 a lactic acid polymer coating c) on the active ingredient coating b), and
 a cationic polymer coating d) on the lactic acid polymer coating c) selected from the group consisting of a polyethylene-imine, chitosan, and a human lactoferrin-derived peptide with a length of 14 to 30 amino acids.

2. The nanoparticle according to claim 1, wherein the active ingredient is a peptide, a protein, or a nucleic acid.

3. The nanoparticle according to claim 1, wherein the active ingredient is a siRNA.

4. The nanoparticle according to claim 1, wherein the human lactoferrin-derived peptide is a peptide with the amino acid sequence according to SEQ. ID. NO:1 KCFQWQRNMRKVRGPPVSCIKR or a sequence that does not differ in more than 8 amino acid positions from SEQ. ID. NO:1.

5. The nanoparticle according to claim 4, wherein, in the amino acid sequence of the human lactoferrin-derived peptide, at least two cysteine residues are present.

6. A pharmaceutical composition, comprising a nanoparticle according to claim 1.

7. A process for preparing the nanoparticle according to claim 1, the process comprising:
 mixing an aqueous solution comprising calcium ions and an aqueous solution comprising phosphate ions and adding an active ingredient, to give a calcium phosphate nanoparticle core a) with the active ingredient coating b) in the form of an inner water phase (WI) for a water-in-oil-in water (WI/O/W2) emulsion;
 adding the lactic acid polymer for the polymer coating c) in an organic solution to the water phase (W1) to give a water-in-oil emulsion (W1/O);
 adding the water-in-oil emulsion (W1/O) to a further water phase (W2) to give the water-in-oil-in-water (W1/O/W2) emulsion;
 removing an organic solvent to give a first dispersion;
 collecting, re-dispersing in water, and drying a solid content of the first dispersion to obtain dried solid particles;
 re-dispersing the dried solid particles in water to obtain re-dispersed solid particles;
 adding a cationic polymer to the re-dispersed solid particles under stirring to obtain a second dispersion which comprises the nanoparticle as a solid content;
 collecting, by centrifugation or tangential flow filtration a solid content of the second dispersion; and
 re-dispersing or drying the solid content of the second dispersion to result in an aqueous dispersion or a dry preparation comprising the nanoparticle.

8. A method of preparing a pharmaceutical composition, the method comprising:
 adding the nanoparticle according to claim 1 to a composition, thereby forming the pharmaceutical composition that comprises the nanoparticle, wherein said pharmaceutical composition is suitable for oral or parenteral delivery to a subject in need thereof.

9. The nanoparticle according to claim 1, which has a polydispersity index in the range of 0 to 0.8.

10. The nanoparticle according to claim 1, wherein the lactic acid polymer of the lactic acid polymer coating c) has at least 10 mol % of polymerized lactic acid or lactide units.

11. The nanoparticle according to claim 1, wherein the lactic acid polymer of the lactic acid polymer coating c) is a lactide-glycolide copolymer.

12. The nanoparticle according to claim 1, wherein the lactic acid polymer of the lactic acid polymer coating c) is a poly(D,L-lactide-co-glycolide) copolymer with an inherent viscosity IV from 0.1-2.0 [dL/g].

13. The nanoparticle according to claim 1, wherein the lactic acid polymer of the lactic acid polymer coating c) is a poly(D,L-lactide-co-glycolide) copolymer with a proportion of D,L-lactide:glycolide in the poly(D,L-lactide-co-glycolide) copolymer from 80:20 to 20:80 parts by weight, where the parts D,L-lactide:glycolide add up to 100 parts (100%).

14. The nanoparticle according to claim 1, wherein the cationic polymer of the cationic polymer coating d) is a polyethylene-imine having a molecular weight ($M_w$) of from 5,000 to 50,000.

15. The nanoparticle according to claim 1, wherein the cationic polymer of the cationic polymer coating d) is chitosan having a molecular weight ($M_w$) of from 20,000 to 250,000 and is acetylized to a degree of 50 to 100%.

16. The nanoparticle according to claim 1, wherein the human lactoferrin-derived peptide is a peptide with the amino acid sequence according to SEQ. ID. NO:1 KCFQWQRNMRKVRGPPVSCIKR or a sequence that does not differ in more than 8 amino acid positions from SEQ. ID. NO:1, provided that the cysteine residues in positions 2 and 19 of SEQ. ID. NO:1 are present.

* * * * *